(12) United States Patent
Moake et al.

(10) Patent No.: US 6,918,293 B2
(45) Date of Patent: Jul. 19, 2005

(54) SYSTEM AND METHOD HAVING RADIATION INTENSITY MEASUREMENTS WITH STANDOFF CORRECTION

(75) Inventors: Gordon L. Moake, Houston, TX (US); Jerome A. Truax, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 10/409,998

(22) Filed: Apr. 9, 2003

(65) Prior Publication Data

US 2004/0200274 A1 Oct. 14, 2004

(51) Int. Cl.$^7$ .............................................. E21B 49/00
(52) U.S. Cl. .................... 73/152.05; 250/254; 250/264; 250/267
(58) Field of Search ........................ 73/152.05, 152.01, 73/152.04; 250/254, 264, 267

(56) References Cited

U.S. PATENT DOCUMENTS

| | | | |
|---|---|---|---|
| 4,129,777 A | * 12/1978 | Wahl et al. | 250/264 |
| 4,909,075 A | * 3/1990 | Flaum et al. | 73/152.05 |
| 5,091,644 A | 2/1992 | Minette | |
| 5,357,797 A | * 10/1994 | Maki, Jr. et al. | 73/152.05 |
| 5,390,115 A | * 2/1995 | Case et al. | 73/152.05 |
| 5,473,158 A | 12/1995 | Holenka et al. | |
| 5,513,528 A | 5/1996 | Holenka et al. | |

OTHER PUBLICATIONS

G.L. Moake, *Definition of an Improved Lithology Factor and a Laboratory Technique for its Measurement*; 29$^{th}$ Annual SPWLA Symposium, San Antonio, Texas, (19 p.); Jun., 1998. (Only p. 1–19).

G.L. Moake, *A New Approach to Determining Compensated Density and $P_e$ Values with a Spectral–Density Tool*; 32$^{nd}$ Annual SPWLA Sympsium, Midland, Texas, (24 p.); Jun. 16–19, 1991. (Only p. 1–24).

* cited by examiner

*Primary Examiner*—Hezron Williams
*Assistant Examiner*—André K. Jackson
(74) *Attorney, Agent, or Firm*—Conley Rose, P.C.

(57) ABSTRACT

We disclose density measurement methods that are accurate over an extended range of standoff distances. One method embodiment includes: a) obtaining a standoff distance, a near detector count rate, and a far detector count rate; b) determining a formation density measurement using near and far detector count rates when the standoff distance is less than a predetermined value; and c) determining the formation density measurement using just the far detector count rate and the standoff distance measurement when the standoff distance is greater than the predetermined value. The method may further include calculating a calibration parameter when the standoff distance is less than the predetermined value. The calibration parameter serves to calibrate a standoff-based correction to the far detector count rate, enabling accurate formation density measurements at large standoff distances. The measurements are made with a rotating logging tool, causing the standoff distance to cycle between large and small values.

14 Claims, 3 Drawing Sheets

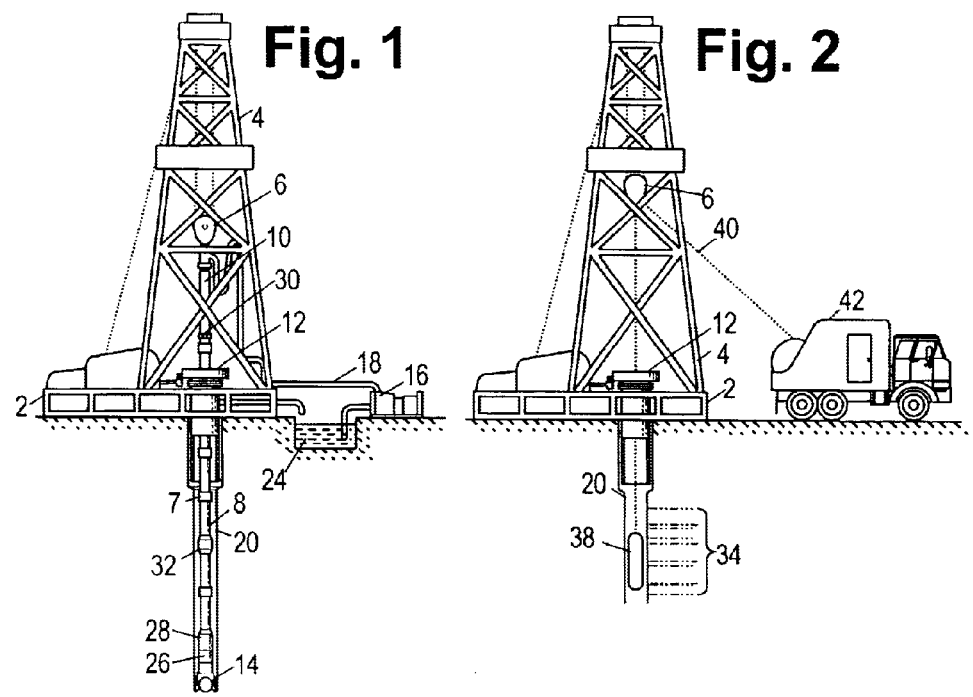
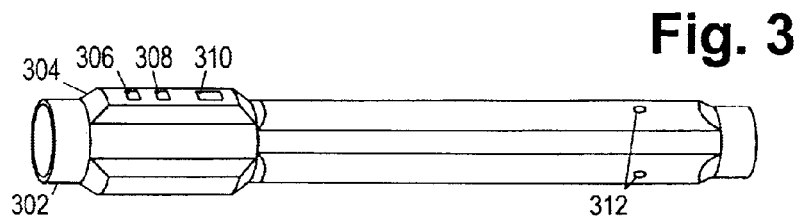
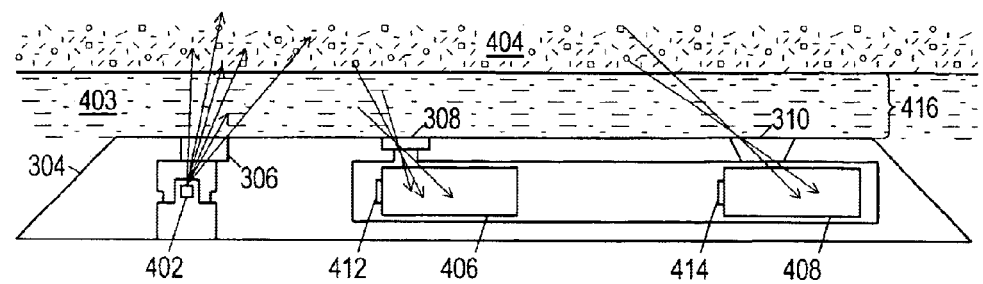

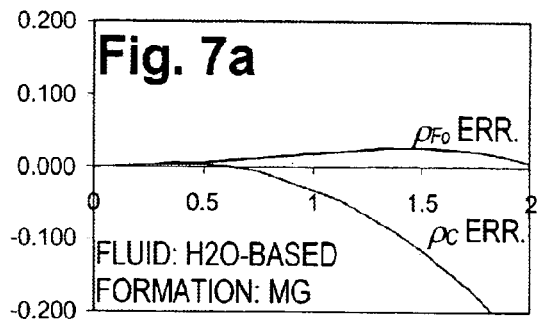
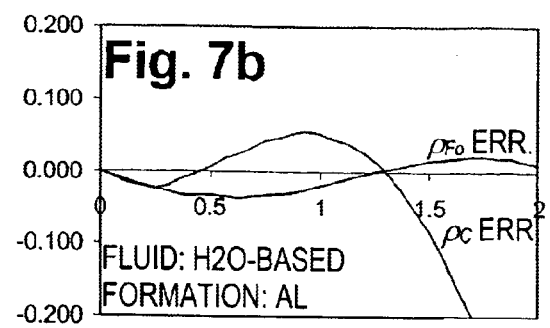
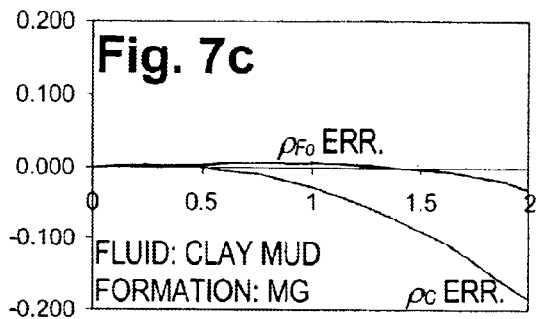
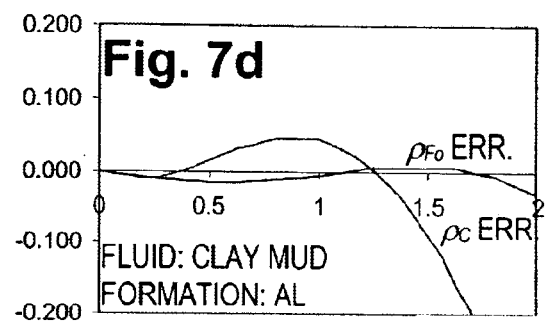
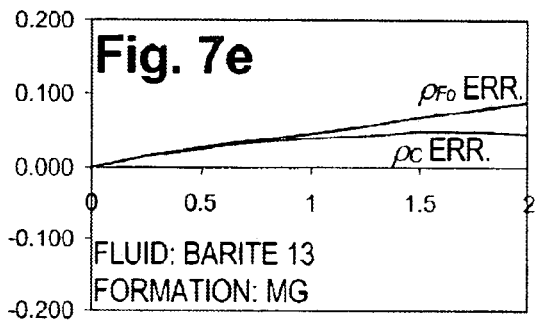
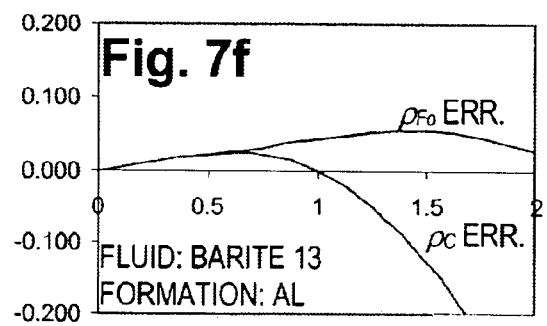
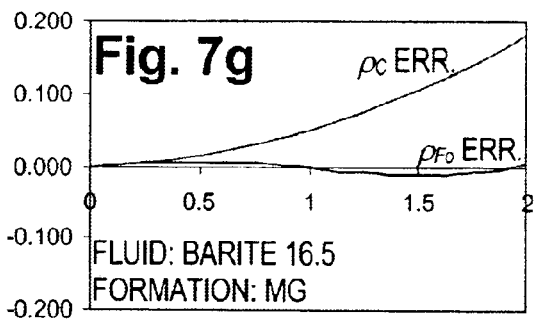
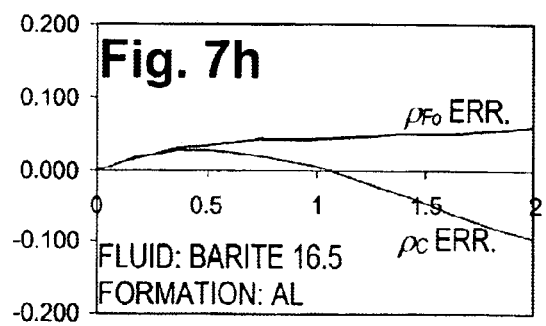
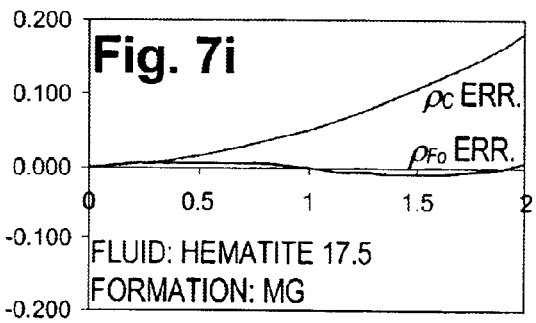
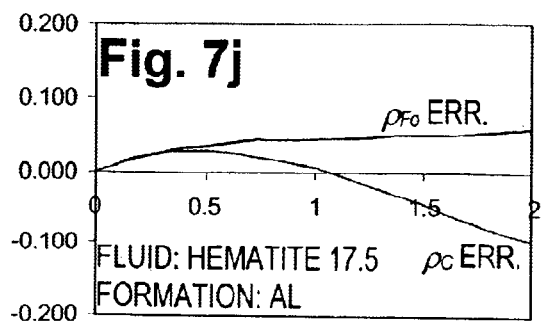

SYSTEM AND METHOD HAVING RADIATION INTENSITY MEASUREMENTS WITH STANDOFF CORRECTION

BACKGROUND

Modern petroleum drilling and production operations demand a great quantity of information relating to parameters and conditions downhole. Such information typically includes characteristics of the earth formations traversed by the borehole, along with data relating to the size and configuration of the borehole itself. The collection of information relating to conditions downhole, which commonly is referred to as "logging", can be performed by several methods.

In conventional wireline logging, a probe (or "sonde") containing formation sensors is lowered into the borehole after some or all of the well has been drilled. The formation sensors are used to determine certain characteristics of the formations traversed by the borehole. The upper end of the sonde is attached to a conductive wireline that suspends the sonde in the borehole. Power is transmitted to the instruments in the sonde through the conductive wireline. Conversely, the instruments in the sonde communicate information to the surface using electrical signals transmitted through the wireline.

An alternative method of logging is the collection of data during the drilling process. Collecting and processing data during the drilling process eliminates the necessity of removing the drilling assembly to insert a wireline logging tool. It consequently allows the driller to make accurate modifications or corrections as needed to optimize performance while minimizing down time. "Measurement-while-drilling" (MWD) is the term for measuring conditions downhole concerning the movement and location of the drilling assembly while the drilling continues. "Logging-while-drilling" (LWD) is the term for similar techniques, which concentrate more on the measurement of formation parameters. While distinctions between MWD and LWD may exist, the terms MWD and LWD often are used interchangeably. For the purposes of this disclosure, the term LWD will be used with the understanding that this term encompasses both the collection of formation parameters and the collection of information relating to the movement and position of the drilling assembly.

In LWD systems, sensors typically are located at the lower end of the drill string. More specifically, the downhole sensors are typically positioned in a cylindrical drill collar positioned near the drill bit. While drilling is in progress these sensors continuously or intermittently monitor predetermined drilling parameters and formation data and transmit the information to a surface detector by some form of telemetry. There are a number of existing and contemplated telemetry systems which may be used to transmit information regarding downhole parameters up to the surface without requiring the use of a wireline.

Of particular interest to the present disclosure are sensors for measuring standoffs, and logging instruments for measuring density. The term "standoff" refers to the distance between the borehole wall and the logging tool. A number of standoff measurement techniques exist in the oilfield industry. One example is a spring-loaded arm that extends from the tool to press against the borehole wall. The extension of the aim indicates the standoff measurement. Another example involves a piezoelectric transducer. The piezoelectric transducer transmits pulses of ultrasonic energy and measures the delay until echoes arrive from the borehole wall. With knowledge of velocity and transit time of the acoustic pulses, a standoff distance can be calculated.

One technique for measuring formation density involves the use of gamma rays. Gamma rays are high-energy photons emitted from an atomic nucleus. Such radiation is typically associated with the decay of radioactive elements. One example of an existing logging instrument for measuring density includes a gamma ray source of cesium-137. The gamma rays from the source travel into the formation where they interact with electrons. The interactions include absorption and scattering. Some of the scattered gamma rays return to detectors in the logging instrument where they are counted and their energy is measured. From the gamma ray measurements, a determination of electron density and lithology type may be made. From these determinations, a standard weight-to-volume density may be calculated.

Closely related techniques for performing porosity measurements involve the use of neutron tools. Neutrons emitted from a neutron source interact with the formation and are scattered back to detectors in the tool. From the detector measurements, a determination of formation porosity may be calculated. Accordingly, both gamma ray tools and neutron tools depend on measurements of radiation intensity.

Radiation intensity measurements are adversely affected by the downhole conditions, and in particular, are adversely affected by drilling fluid in the borehole and the relative geometry of the borehole. To compensate for these adverse effects, a pair of detectors may be included in the logging tool and their measurements combined. See, e.g., G. L. Moake, "A New Approach to Determining Compensated Density and Pe Values With a Spectral-Density Tool", SPWLA Logging Symposium, paper 91-Z, 1991, which is hereby incorporated by reference. However, existing compensation techniques generally fail at larger standoff distances, so existing radiation intensity measurement tools are designed to remain in close contact with the borehole wall. A technique that compensates radiation intensity measurements made during large standoffs is desirable as it would allow for more versatile operation of the radiation intensity measurement tool.

SUMMARY

Accordingly there is disclosed herein radiation intensity measurement methods that are accurate over an extended range of standoff distances. In one embodiment, the method includes: a) obtaining a standoff distance, a count rate from a near detector, and count rate from a far detector; b) determining a formation property measurement using near and far detector count rates when the standoff distance is less than a predetermined value; and c) determining the formation property measurement using standoff measurements and the far detector count rate when the standoff distance is greater than the predetermined value. The method may further include calculating a calibration parameter when the standoff distance is less than the predetermined value. The calibration parameter serves to calibrate the standoff-based correction for far detector count rates to enable accurate formation property measurements without using the near detector. In a preferred embodiment, the measurements are made with a logging tool that rotates, and accordingly, the standoff distance may cycle between large and small values.

BRIEF DESCRIPTION OF THE DRAWINGS

A better understanding of the present invention can be obtained when the following detailed description of the preferred embodiment is considered in conjunction with the following drawings, in which:

FIG. 1 shows a representative logging-while-drilling (LWD) configuration;

FIG. 2 shows a representative wireline-logging configuration;

FIG. 3 shows one logging tool embodiment;

FIG. 4 shows a partial cross-section of the logging tool embodiment;

FIGS. 7a–7j show graphs of density measurement errors as a function of standoff in different formation and fluid combinations.

Figure 5:
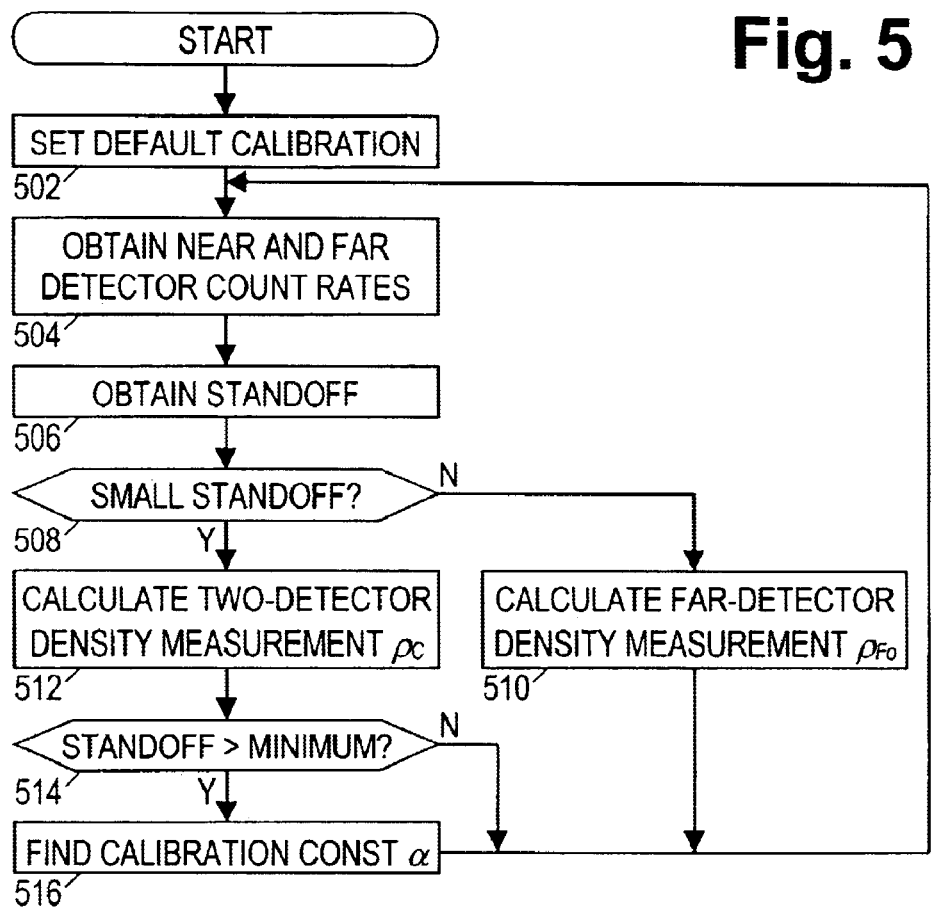
FIG. 5 shows a flowchart of one formation property measurement method embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

NOTATION AND NOMENCLATURE

Certain terms are used throughout the following description and claims to refer to particular system components and configurations. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections. The terms upstream and downstream refer generally, in the context of this disclosure, to the transmission of information from subsurface equipment to surface equipment, and from surface equipment to subsurface equipment, respectively. Additionally, the terms surface and subsurface are relative terms. The fact that a particular piece of hardware is described as being on the surface does not necessarily mean it must be physically above the surface of the earth; but rather, describes only the relative placement of the surface and subsurface pieces of equipment.

DETAILED DESCRIPTION

Turning now to the figures, FIG. 1 shows a representative well during drilling operations. A drilling platform 2 is equipped with a derrick 4 that supports a hoist 6. Drilling of oil and gas wells is carried out with a string of drill pipes connected together by "tool" joints 7 so as to form a drill string 8. The hoist 6 suspends a kelly 10 that is used to lower the drill string 8 through rotary table 12. Connected to the lower end of the drill string 8 is a drill bit 14. The bit 14 is rotated by rotating the drill string 8 or by operating a downhole motor near the drill bit. The rotation of the bit 14 extends the borehole.

Drilling fluid is pumped by recirculation equipment 16 through supply pipe 18, through drilling kelly 10, and down through the drill string 8 at high pressures and volumes to emerge through nozzles or jets in the drill bit 14. The drilling fluid then travels back up the hole via the annulus between the exterior of the drill string 8 and the borehole wall 20, through the blowout preventer (not specifically shown), and into a mud pit 24 on the surface. On the surface, the drilling fluid is cleaned and then recirculated by recirculation equipment 16. The drilling fluid cools the drill bit 14, carries drill cuttings to the surface, and balances the hydrostatic pressure in the rock formations.

Downhole instrument sub 26 is coupled to a telemetry transmitter 28 that communicates with the surface to provide telemetry signals and receive command signals. A surface transceiver 30 may be coupled to the kelly 10 to receive transmitted telemetry signals and to transmit command signals downhole. One or more repeater modules 32 may be provided along the drill string to receive and retransmit the telemetry and command signals. The surface transceiver 30 is coupled to a logging facility (not shown) that may gather, store, process, and analyze the telemetry information.

FIG. 2 shows a representative well during wireline logging operations. The derrick 4 is not necessary for wireline logging, but is typically present throughout the drilling process. The drill string has been removed from the borehole to allow a sonde 38 to be lowered by wireline 40 into the well. Typically, the sonde 38 is lowered to the bottom of the region of interest and subsequently pulled upward at a constant speed. During the upward trip, the sonde 38 performs measurements on the formations 34 adjacent to the borehole as the sonde passes by. The measurement data are communicated to a logging facility 42 for storage, processing, and analysis.

During the wireline logging operations, the borehole is filled with a fluid that balances the pressure in the formation and preserves the integrity of the borehole. A number of fluid types may be used, depending on considerations of cost, environment, and formation type. The fluids may be water-based or oil-based, and are generally formulated with weighting agents to customize the fluid density.

For clarity, the following description will focus on embodiments of a gamma ray tool for density logging. The principles described will apply equally well to neutron tools, though minor changes to the details may be needed to accommodate the different implementation. Any such changes are expected to be readily perceived by those of ordinary skill in the art.

FIG. 3 shows an illustrative example of a density logging tool configured for use as a logging-while-drilling (LWD) tool. Logging tool 302 has an external protrusion 304 that houses a gamma ray source behind source window 306, and two gamma ray detectors behind windows 308, 310. The detectors are positioned at different distances from the source and shielded so as to detect only gamma rays that arrive from the formation. The tool is configured to measure predominately in one direction. The tool may also include a set of ultrasonic transducers 312 configured to measure the size of the borehole and the position of the tool within the borehole.

In the preferred embodiment, an ultrasonic transducer 312 aligned With the face (windows) of the density tool measures a standoff distance between the borehole wall and the face of the density tool. In an alternative embodiment, multiple ultrasonic transducers 312 are used to measure the borehole geometry and the position of the tool within the borehole. From these measurements, the standoff distance can be determined. Such standoff measurement approaches may advantageously avoid increasing the diameter of the tool, and the lack of moving parts increases reliability. At least one transducer 312 is preferably mounted in line with the face of the tool and as close to the windows as possible.

The beam from each ultrasonic transducer should be focused so as to provide the best spatial resolution possible that is consistent with traveling round trip through several inches of drilling fluid. In an LWD environment where the tool may be close to the borehole wall and rotating, the use of multiple, azimuthally-spaced transducers is preferred to ensure that a the transmitted signal is reflected back to a receiver, but a single transducer may alternatively be used in this and other environments. Each ultrasonic transducer is preferably pulsed frequently enough so that small changes in the standoff can be monitored. In wireline logging, that may be as often as 12 times for every foot of travel, which could be as fast as 12 times a second. In LWD where the tool is rotating, it may be advantageous to measure the standoff as frequently as 100 times in one rotation, which could be as frequent as 300 times a second. As an alternative to such a high sampling rate, a lower sampling rate may be used in conjunction with interpolation.

If the tool is flush against the borehole wall, either detector can be used to provide an accurate measure of the formation density. However, in a real-world environment, it is unlikely that the tool will be flush against the borehole wall. The borehole wall may be rugose (washed out in places). There may be a mudcake (a viscous or semi-solid layer of drilling fluid) on the borehole wall. The position of the tool within the borehole may keep the tool face undesirably far from the borehole wall. Any of these adverse conditions may prevent the tool from making good contact with the borehole wall.

In wireline logging, a density tool is typically deployed beyond the main tool string by a mechanism designed to push the pad against the wall, thereby minimizing standoff and mudcake thickness. This mechanism is costly, and it creates a risk of getting the tool stuck downhole. Further, the mechanism is not foolproof, so there is an additional risk of improper mechanical operation.

In LWD, the drilling string and attached logging tools are usually rotating, making it impractical to mechanically force the density tool against the wall. The drill string tends to be near the borehole wall, so that as the tool rotates, at least some measurements are made with a small standoff. One approach in these circumstances is to selectively retain measurements made with a small standoff. However, there is no guarantee that such a condition will always exist. Also, there are times when the drill string is drilling without rotating, and the density tool may be constantly at a large distance from the borehole wall. In that case, the density measurement would have unacceptably-large errors.

In LWD (and perhaps eventually in wireline logging), the logging tool may be configured to perform density imaging as the tool rotates. Density imaging involves making formation density measurements around the circumference of the borehole wall and along the length of the borehole. This may be useful for ascertaining the dip of formation beds and for steering the drill string. Because the tool tends to be near one side of the borehole, at least some of the measurements in density imaging will be made with a large standoff.

The measurements from the two detectors can be combined to compensate for these adverse conditions, and to provide an accurate measure of the formation density whenever the tool is not far from the borehole wall. As discussed in the background, however, existing compensation techniques fail at larger standoffs. The disclosed compensation method may be used to advantageously extending the accuracy of measurements at large standoffs.

FIG. 4 shows a cross-sectional view of the protrusion 304 during an illustrative measurement. The body of protrusion 304 is preferably made of steel, and may include "windows" 306, 308, and 310 that are relatively (as compared with the rest of the housing) transparent to gamma rays. The windows may simply be regions of reduced housing thickness, or they may be made using relatively transparent materials such as titanium (which is strong while having a relatively low density) or beryllium oxide (which is a low-atomic number material). Of course a combination of reduced thickness and relatively transparent material may also be used. In LWD tools, titanium is preferred for all windows, while in wireline titanium is preferred for all windows except the near detector window for which beryllium oxide is preferred.

Tool 302 includes a gamma ray source 402 such as, e.g., a 1.5 Curie cesium-137 source. Gamma rays pass from source 402 through window 306, through any intervening fluid 403, and into formation 404. Electrons in the formation (and fluid) interact with the gamma rays, absorbing some and scattering some. Some of the scattered gamma rays travel back from the formation through window 308 and into detector 406, and similarly through window 310 into detector 408.

Detectors 406, 408 may be sodium iodide detectors. Crystals in such detectors emit a scintillation of light when struck by a gamma ray. The brightness of the scintillation is related to the energy of the gamma ray. The scintillations are converted into electrical pulses by a photo-multiplier tube. The electrical pulses can be processed by electronic circuitry to form digital measurement data. The digital measurement data may be combined with other pulse measurements to form logging information which is then transmitted to a surface facility for storage and analysis. The logging information preferably comprises an energy spectrum for each detector. The energy spectrum may be stated in the form of a number of gamma rays received during a time interval having an energy in each energy "bin". (Energy bins are predetermined energy ranges.) In an alternative embodiment, the logging information may be a simple overall count rate.

Small gamma ray sources 412, 414 may be placed on the detectors as calibration standards. The electronics may use the calibration standards to compensate for temperature-induced and count-rate induced variations. The electronics preferably also include temperature sensors to help compensate for the temperature variation.

FIG. 4 also shows the standoff distance 416. In the preferred embodiment, the standoff distance is calculated as the distance between the windows 308, 310 and the borehole wall.

A preferred standoff correction technique is now described. This technique may be performed downhole by the tool, or may be performed in a surface facility during the analysis of logging information. The following variables are used:

| | |
|---|---|
| N | Near-detector count rate |
| F | Far-detector count rate |
| $F_0$ | Far-detector count rate corrected to remove standoff effects |
| ρN | Density computed from N assuming no standoff |
| ρF | Density computed from F assuming no standoff |
| ρ | Measurement of the formation density |
| S | Standoff |
| $a_i$, $b_i$, $c_i$, β | Calibration parameters determined in shop |
| α | Calibration parameter determined dynamically |

Various embodiments are now described for making density measurements at small standoffs. In a first embodiment, an overall count rate N as measured by the near detector (e.g. detector 406) is converted into a density measurement. The conversion may be expressible as $$\rho_N = a_0 + a_1 \ln(N), \quad (1)$$

where $a_0$ and $a_1$ are predetermined calibration parameters. Other conversions are possible and may be preferred. Similarly, an overall count rate F as measured by the far detector (e.g. detector 408) is convertible into a density measurement. The conversion may be expressible as $$\rho_F = b_0 + b_1 \ln(F), \quad (2)$$

From the near and far density measurements, a density difference x may be determined:

$$x = \rho_F - \rho_N \quad (3)$$

and this difference may be used to determine a density correction Δρ. The density correction is expressible as:

$$\Delta\rho = \begin{cases} c_1 x + c_2 x^2 & \text{if } x \geq 0 \\ c_3 x & \text{if } x < 0. \end{cases} \quad (4)$$

The density correction can be combined with the far detector density measurement to provide a formation density measurement $\rho_C$ that is accurate for small standoffs (e.g. standoffs less than half an inch):

$$\rho_C = \rho_F + \Delta\rho. \quad (5)$$

In a second embodiment, counts are used from multiple detectors (denoted by index i) and multiple energy windows (denoted by index j). The variable $N_{ij}$ represents the count from energy window j of detector i. The second embodiment determines a formation density measurement for small standoffs by solving a set of simultaneous equations expressible as:

$$\ln(N_{ij}) = a_{0ij} + a_{1ij}\rho + a_{2ij}\rho^2 + a_{3ij}\rho^3 + a_{5ij}L, \quad (6)$$

where $a_{kij}$ are predetermined calibration parameters, and L is a lithology factor L, which may be calculated from the count rate energy distribution. Certain methods for determining a lithology factor are described in G. L. Moake, "Definition of an improved lithology factor and a laboratory technique for its measurement", 29th Annual SPWLA Symposium, San Antonio, Tex., June 1988, which is hereby incorporated herein by reference. In a third embodiment, the conversion may be expressible as $$\ln(N_{ij}) = a_{0ij} + a_{1ij}\rho + a_{2ij}\rho^2 + a_{3ij}\rho^3 + a_{5ij}L + a_{6ij}(\rho - \rho_m)t + a_{7ij}(L - L_m)t, \quad (7)$$

where t is a mudcake thickness, $\rho_m$ is mudcake density, and $L_m$ is the mudcake lithology factor. The preferred embodiment may use more than one conversion as explained further below. Some of these formulations may benefit from the use of iterative numerical solution techniques.

For large standoffs, the density calculation is modified. In the first embodiment, a corrected far detector count rate $F_0$ is determined. (This is the count rate that should be observed if the standoff were zero.) The correction is expressible as $$F_0 = \begin{cases} Fe^{-\alpha S} & \text{if } S \leq S_t \\ Fe^{-\alpha[S_t - \beta(S - S_t)^2]S} & \text{if } S > S_t, \end{cases} \quad (8)$$

where α is a calibration parameter that accounts for effects of the drilling fluid, S is the standoff in inches, and $S_t$ is a predetermined standoff threshold. β may be a predetermined, tool-dependent constant. For one tool, β was preferably 0.12. The standoff threshold $S_t$ may preferably be about one inch. The corrected far detector count rate $F_0$ may be used in accordance with equation (2) to determine a far detector density measurement $\rho_{F_o}$ which is used as an estimate of the formation density ρ:

$$\rho = \begin{cases} \rho_C & \text{for small standoff } S \\ \rho_{F_0} & \text{for large standoff } S. \end{cases} \quad (9)$$

The dividing line between small and large standoffs may be adjusted based on experience, but is expected to be about half an inch.

The calibration parameter α is preferably set dynamically, i.e. during normal operation of the tool. The calibration parameter may be determined from a set of one or more density measurements. The set preferably includes only the most recently-taken measurement(s) at standoff distances within a predetermined window, i.e. below a predetermined threshold value and above a predetermined minimum value. To set the calibration parameter, the far detector density measurement $\rho_{F_o}$ is set equal to the calculated formation density ρ, and the corresponding "corrected far detector count rate" $F_0$ is determined. The count rate $F_0$ may be determined in accordance with equation (2). With knowledge of the measured far detector count rate F and the corrected far detector count rate $F_0$, the calibration parameter α can be determined in accordance with equation (8). A filtering technique (e.g. a moving average filter) may be used to smooth variations in the calibration parameter.

In the second and third embodiments, the calculation of densities at a large standoff distance may be made as before, but omitting the counts from the nearest detector and using a different set of coefficients. If the tool only includes two detectors, then it may be preferred that the counts in the various energy windows from the far detector be individually scaled in accordance with equation (8) before performing the density calculation. The calibration parameter for each energy window may be dynamically calculated as before. That is, when the standoff distance is within a predetermined window, the calculated formation density is used to determine expected count rates from the far detector. (The expected count rates are those count rates predicted using the reduced set of equations that you would be using at large standoff distances.) The calibration parameters are then determined by comparing the expected count rates to the measured count rates.

FIG. 5 shows a flow diagram of a preferred density measurement method. Beginning in block 502, the tool sets a default calibration parameter. This parameter may be an average value determined from experience or model predictions. In block 504, the tool measures the near and far detector count rates N,F. These are preferably the number of counts within a predetermined energy window, but overall count rates may also be used. In one embodiment, the near detector measurements are made within an energy range of 240–380 keV, and the far detector measurements are made within an energy range of 180–380 keV.

In block 506, the standoff S is determined, and in block 508 the standoff is compared to a predetermined threshold. If the standoff exceeds the threshold, then in block 510 the formation density is estimated without the near detector count rates, e.g., using a far detector density measurement $\rho F_o$. Control then returns to block 504 to obtain the next set of measurements.

If in block 508 the standoff S is less than the threshold, then in block 512, the formation density is estimated using measurements from all the detectors, e.g. by calculating the two-detector density measurement $\rho_C$. In block 514 a check is made to determine whether the standoff distance is greater than a minimum value, and if it is not, then control returns to block 504. Otherwise, the calibration parameter $\alpha$ is calculated in block 516. The calibration parameter may be recalculated from scratch each time a small standoff is measured, or alternatively, a filtering or least-squares technique may be used to reduce "noisy" variation of the calibration parameter.

Figure 6:
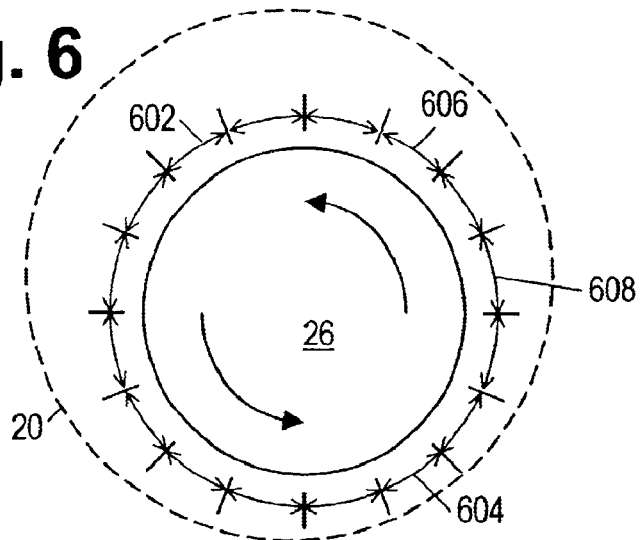
FIG. 6 shows angular sections which may be used for wellbore imaging.

The disclosed technique may be particularly suited to imaging LWD. In LWD, it is often desirable to generate an image of the formation density that represents the changing formation density measured by the tool as the tool rotates around the borehole. Towards this end, the borehole is divided up into N different sections, with N=16 being a good compromise between angular resolution and statistical precision. FIG. 6 shows in schematic form a cross-section of the borehole 20 with a rotating tool 26 therein. (Note that the drawing is not to scale.) The borehole may be highly deviated or even horizontal, causing a significant de-centering of the tool 26. The tool has an ultrasonic transducer that measures standoff as the tool rotates, and it is clear from the figure that the standoff changes as the face of the tool rotates. The density measurement tool 26 also determines gamma ray count rates as the tool rotates.

Magnetometers may be used to determine the orientation of the tool 26 at any given instant. As the tool rotates, the measurements are associated with one of N angular bins as shown in FIG. 6. Measurements from the density tool 26 are sampled in time increments that are small compared to the time spent in any one angular section. For example, if the tool string is rotating at 2 Hz and each revolution is divided into 16 sections of 22.5 degrees each, the tool will spend, on average, 31.25 msec in each section during a revolution. Thus, it is preferable that data be sampled in 10 msec intervals or smaller. Each density measurement should have a corresponding measurement of standoff and tool orientation. The tool orientation is used to determine to which angular section the data corresponds, and the average value of the detector measurements and standoff measurement for that angular section is updated. After a given amount of time, say 10 seconds, the average values of each section are combined to compute formation density, one value for each angular section at that borehole "depth". They can also be combined to obtain other quantities, such as the photoelectric value Pe, which is characteristic of the formation's elemental composition.

To calibrate the standoff correction for the far detector, an angular section may be chosen that has an average standoff that is moderately large yet still small enough that the two-detector density measurement is expected to be accurate. The two-detector density is computed, and the calibration parameters are determined such that the far-detector density is equal to the two-detector density in this section. The other angular sections may then be processed as follows. If the average standoff for that section is smaller than or equal to the standoff of the first section, the two-detector algorithm is used. Otherwise, the far detector measurements are corrected for standoff using the parameters determined during the calibration, and then used to compute formation density with equations that are valid when no standoff is present. If the standoff is unusually large, there may be other correction components used to account for a diminished sensitivity of the far detector to the formation density. An image is then obtained from the density values in the different angular sections in the normal manner.

In FIG. 6, bin 602 represents the bin having the largest standoff, and bin 604 represents the bin having the smallest standoff. If it is assumed that bin 604 has a standoff below the standoff threshold, and bin 602 has a standoff above the threshold, then as the tool rotates from bin 604 to bin 602, the density calculation will switch from the two-detector calculation to the far-detector calculation at some intermediate bin such as bin 606. Before or at the switchover bin, a calibration is performed, e.g., in bin 608. In the following comparisons, the calibration is assumed to be performed when the average standoff of the bin is 0.25 inches.

Data used in the comparisons of FIGS. 7a–7j was acquired with a real tool. It was characterized using measured data, as described below.

Acquisition Details: Data was acquired with an LWD tool in aluminum (Al) and magnesium (Mg) characterization blocks. These blocks had densities of 2.60 and 1.68 g/cc, which spans much of the density range that is normally logged. The measurements were repeated with a wide variety of drilling fluids. Standoffs ranging from 0 to 2 inches were used. For the purposes of illustration, a simple density algorithm using count rates from the 240–380 keV (near detector) and 180–340 keV (far detector) energy windows was used to compute density. Compensation for the two-detector density was achieved using the standard spine-and-ribs method. Since the two-detector algorithm will only be used for small standoffs, the rib was computed only from standoffs of a half inch or less. A quadratic rib was used for positive corrections and a linear one for negative corrections. Density-dependent ribs were used, so that one set of ribs was used for aluminum, and one for magnesium.

Comparison: FIGS. 7a through 7j show density error (in g/cc) as a function of standoff (in inches). Each figure corresponds to a given fluid and "formation". Each figure shows both the error curve for the two-detector density calculation, and the error curve for the far detector density calculation. The two "formations" are the aluminum (Al) and magnesium (Mg) characterization blocks, having densities of 2.60 g/cc and 1.68 g/cc, respectively. Five fluids are considered: a water-based drilling fluid, a clay mud, a barite-weighted fluid at 13 lbm/gal, a barite-weighted fluid at 16.5 lbm/gal, and a hematite-weighted fluid at 17.5 lbm/gal. Standoffs ranging from 0 to 2 inches were used, although the amount of standoff that would be seen in a well depends on the borehole diameter, the diameter of the tool being used, and the tool standoff in the borehole.

An examination of the figures shows that on balance, the density error is smaller for the far-detector calculation than the two-detector calculation at standoffs greater than one inch. Further, the errors are small enough so as to allow for reasonable measurements out to at least two inches. The greatest source of error in the far-detector density may be the calibration value, which is obtained from the two-detector density. To minimize the error in calibration value, a more accurate two-detector density calculation may be desired.

In conclusion, methods for performing density calculations at large standoffs have been disclosed. Density measurements made at small standoffs are used to calibrate a far detector density measurement, and the far detector density measurement is then accurate at large standoffs. This approach is expected to be particularly suited for density imaging by a LWD tool, and is further expected to work well for wireline logging and sliding (non-rotational) LWD. The techniques disclosed herein may also be advantageously applied to neutron tools making formation porosity measurements.

When an LWD tool is sliding, the tool is often laying on or near the bottom of the borehole. The detector windows may be pointing down, so that standoff is small and a good two-detector density is computed. However, the windows, could also be pointing up. Depending on the size of the borehole, there could be a large standoff between the tool and borehole wall, such that the two-detector density would not be very accurate. In that case, it would be advantageous to use the standoff-corrected far-detector density, as long as the calibration parameters have been determined. The calibration may have been performed during previous rotation of the tool, perhaps using an average of the standoff-calibration factors measured over the last several minutes of rotation.

In wireline logging, it is sometimes desirable to have tool that does not require a deployment arm for pressing the sensor against the borehole wall. Instead, a "centralizer" or bowspring configuration may be used to keep the entire tool near a desired position in the borehole. The tool may be maintained near one side of the borehole, e.g. generally within half an inch of the wall. When the standoff is small, the two detector density measurement may be performed, and a calibration established. When the standoff exceeds a predetermined threshold, the calibrated far detector density measurement may be performed.

Numerous variations and modifications will become apparent to those skilled in the art once the above disclosure is fully appreciated. It is intended that the following claims be interpreted to embrace all such variations and modifications.

What is claimed is:

1. A density measurement method comprising:
   obtaining a standoff distance, a count rate from a near detector, and a count rate from a far detector;
   determining a formation density measurement using count rates from the near and far detectors when the standoff distance is less than a predetermined value; and
   determining the formation density measurement using the count rate from the far detector and not the count rate from the near detector when the standoff distance is greater than the predetermined value.

2. The method of claim 1, further comprising:
   calculating a calibration parameter when the standoff distance is less than the predetermined value, wherein the calibration parameter calibrates said step of determining the formation density measurement when the standoff distance is greater than the predetermined value.

3. A density measurement method comprising:
   obtaining a standoff distance a count rate from a near detector, and a count rate from a far detector;
   determining a formation density measurement using count rates from the near and far detectors when the standoff distance is less than a predetermined value;
   determining the formation density measurement using the count rate from the far detector and not the count rate from the near detector when the standoff distance is greater than the predetermined value; and
   calculating a calibration parameter when the standoff distance is less than the predetermined value, wherein the calibration parameter calibrates said step of determining the formation density measurement when the standoff distance is greater than the predetermined value;
   wherein said step of determining the formation density measurement when the standoff distance is greater than the predetermined value includes;
   adjusting the count rate from the far detector to account for drilling fluid effects.

4. The method of claim 3, wherein said adjusting is in accordance with $$F_0 = \begin{cases} Fe^{-\alpha S} & \text{if } S \leq S_t \\ Fe^{-\alpha[S_t-\beta(S-S_t)^2]S} & \text{if } S > S_t, \end{cases}$$

wherein F is the far detector count rate, $F_0$ is the adjusted far detector count rate, $\alpha$ is the calibration parameter, $\beta$ is a predetermined constant, S is the standoff distance, arid $S_t$ is a threshold standoff.

5. The method of claim 4, wherein said step of determining the formation density measurement when the standoff distance is greater than the predetermined value includes:
   determining the formation density $\rho$ in accordance with $$\ln(F_0) = b_0 + b_1\rho + b_2\rho^2 + b^{3\rho^3} + b_5 L$$

where $b_1$ are predetermined calibration constants, and L is a lithology factor determined from a relationship between count rates in different energy windows.

6. A method of imaging a borehole, the method comprising:
   rotating a logging tool as the logging tool traverses a borehole;
   making near count rate measurements, far count rate measurements, and standoff measurements as the logging tool rotates;
   associating the measurements with borehole surface pixels, wherein the borehole surface pixels are defined by angular sections of the borehole and axial position of the tool in the borehole; and
   calculating a formation property for each pixel, wherein the formation property calculation depends on the standoff measurements,
   wherein said calculating includes determining a formation density from the measurements associated with the borehole surface pixel, and
   wherein the formation density is determined using a count rate from a near detector when standoff for the borehole surface pixel is below a predetermined value, and wherein the formation density is determined without using a count rate from the near detector when standoff for the borehole surface pixel is above the predetermined value.

7. A method of imaging a borehole, the method comprising:
  rotating a logging tool as the logging tool traverses a borehole;
  making near count rate measurements, far count rate measurements, and standoff measurements as the logging tool rotates;
  associating the measurements with borehole surface pixels, wherein the borehole surface pixels are defined by angular sections of the borehole and axial position of the tool in the borehole;
  calculating a formation property for each pixel, wherein the formation property calculation depends on the standoff measurements, and wherein said calculating includes determining a formation density from the measurements associated with the borehole surface pixel; and
  determining a calibration parameter value for use when the formation density is determined without using a count rate from the near detector, said determining of a calibration parameter being performed when standoff for the borehole surface pixel is approximately equal to a predetermined quantity.

8. A method of imaging a borehole, the method comprising:
  rotating a logging tool as the logging tool traverses a borehole;
  making near count rate measurements, far count rate measurements, and standoff measurements as the logging tool rotates;
  associating the measurements with borehole surface pixels, wherein the borehole surface pixels are defined by angular sections of the borehole and axial position of the tool in the borehole;
  calculating a formation property for each pixel, wherein the formation property calculation depends on the standoff measurements, and wherein said calculating includes determining a formation density from the measurements associated with the borehole surface pixel; and
  determining a calibration parameter value during each rotation of the logging tool at a last borehole surface pixel having a standoff below a predetermined quantity.

9. A method of density logging that comprises:
  moving a tool through a borehole in a formation, wherein the tool includes a radiation source;
  measuring a near radiation intensity detected at a first detector near the radiation source;
  measuring a far radiation intensity detected at a second detector more distant from the radiation source than the first detector;
  measuring a standoff distance between the tool and a wall of the borehole; and
  selecting one of a set of formation density-related calculations, wherein the calculation selected when the standoff distance is greater than a predetermined value determines the formation-related density using a calibration parameter, the far radiation intensity, and standoff distant, wherein the formation-related density $\rho$, is calculated so as to be in accordance with $$F_0 = \begin{cases} Fe^{-\alpha S} & \text{if } S \leq S_t \\ Fe^{-\alpha[S_t - 0.12(S-S_t)^2]S} & \text{if } S > S_t \end{cases} \text{ and}$$

$$\ln(F_0) = b_0 + b_1\rho + b_2\rho^2 + b_3\rho^3 + b_5 L,$$

wherein F is the far radiation intensity, $\alpha$ is the calibration parameter, S is the standoff distance, and $S_t$ is a threshold standoff, $b_1$ are predetermined calibration constants, and L is a lithology factor determined from a relationship between count rates in different energy window.

10. A method of density logging that comprises:
  moving a tool through a borehole in a formation, wherein the tool includes a radiation source;
  measuring a near radiation intensity detected at a first detector near the radiation source;
  measuring a far radiation intensity detected at a second detector more distant from the radiation source than the first detector;
  measuring a standoff distance between the tool and a wall of the borehole;
  selecting one of a set of formation density-related calculations, wherein the calculation selected when the standoff distance is greater than a predetermined value determines the formation-related density using a calibration parameter, the far radiation intensity, and standoff distance; and
  when the standoff distance is less than the predetermined value:
    selecting a different one of said set of formation density-related calculations, wherein said different calculation determines the formation-related density using the near radiation intensity and the far radiation intensity; and
    calculating the calibration parameter using both the near radiation intensity and the far radiation intensity.

11. The method of claim 10, further comprising:
  rotating the tool, thereby causing the standoff distance to cycle between values less than the predetermined value and values greater than the predetermined value.

12. The method of claim 11, further comprising associating radiation intensity measurements with angular sections of the borehole.

13. The method of claim 12, further comprising determining an average standoff distance for each angular section.

14. The method of claim 11, wherein said calculating a calibration parameter is performed no more than once for each rotation, and wherein said the calibration parameter is calculated using measurements associated with an angular section having a greatest average standoff distance that is less than the predetermined value.

* * * * *